United States Patent [19]

Nishihira et al.

[11] Patent Number: 6,018,072
[45] Date of Patent: Jan. 25, 2000

[54] PROCESS FOR PRODUCING A DIARYL OXALATE

[75] Inventors: Keigo Nishihira; Shuji Tanaka; Yuki Nishida; Satoru Fujitsu, all of Ube, Japan

[73] Assignee: Ube Industries, Ltd., Ube, Japan

[21] Appl. No.: 08/875,823

[22] PCT Filed: Dec. 12, 1996

[86] PCT No.: PCT/JP96/03636

§ 371 Date: Aug. 7, 1997

§ 102(e) Date: Aug. 7, 1997

[87] PCT Pub. No.: WO97/21660

PCT Pub. Date: Jun. 19, 1997

[30] Foreign Application Priority Data

Dec. 12, 1995 [JP] Japan .................................. 7-323181

[51] Int. Cl.$^7$ .................................................. C07C 69/34
[52] U.S. Cl. ............................................................ 560/146
[58] Field of Search .............................................. 560/146

[56] References Cited

U.S. PATENT DOCUMENTS 3,471,549  10/1969  Hülsmann .
4,451,664  5/1984  Ranade .
4,482,732  11/1984  Ranade .
4,482,733  11/1984  Ranade .

FOREIGN PATENT DOCUMENTS 56-2541  1/1981  Japan .
56-8019  2/1981  Japan .
57-47658  10/1982  Japan .

*Primary Examiner*—Samuel Barts
*Attorney, Agent, or Firm*—Finnegan, Henderson, Farabow, Garrett & Dunner, L.L.P.

[57] ABSTRACT

The present invention relates to a process for producing a diaryl oxalate, characterized in that an alkylaryl oxalate is subjected to a disproportionation reaction in the presence of a disproportionation catalyst, thereby to produce a diaryl oxalate while removing a by-product comprising a dialkyl oxalate.

The production process of the present invention is advantageous in that the kinds of the by-products are fewer than that in conventional production process for diaryl oxalate, and thus can be practically utilized in industry, and the diaryl oxalates such as diphenyl oxalate, produced by the production process of the present invention are very important industrial materials for producing chemical products such as carbamates.

10 Claims, 2 Drawing Sheets

PROCESS FOR PRODUCING A DIARYL OXALATE

This is a 371 of application PCT/JP96/03636 filed Dec. 12, 1996.

TECHNICAL FIELD

The present invention relates to a process for producing a diaryl ester of oxalic acid (a diaryl oxalate), for example, diphenyl oxalate (which will be abbreviated to DPO hereinafter) by disproportionation of an alkylaryl ester of oxalic acid (for example, an alkylphenyl oxalate) used as a starting material. In the process of the present invention, an alkylaryl oxalate (for example, an alkylphenyl oxalate) produced by an ester interchange reaction of a dialkyl ester of oxalic acid (a dialkyl oxalate) with a phenol compound is used as a starting material, and a diaryl oxalate, for example, DPO is produced by disproportionation of the alkylaryl oxalate.

Diaryl oxalates such as diphenyl oxalate are very important industrial materials for the production of chemical products such as carbamates.

BACKGROUND ART

As processes for producing diaryl oxalate, (1) a method in which oxalic acid and a phenol compound are directly esterified by heating them at 100 to 130° C. in an organic solvent in the presence of a esterification catalyst, as disclosed in Japanese Examined Patent Publication No. 52-43, 826; (2) a method in which a dialkyl oxalate is reacted with a diaryl carbonate, as disclosed in Japanese Examined Patent Publication No. 56-8,019 and Japanese Unexamined Patent Publication No. 49-42,621, and (3) a method in which a dialkyl oxalate is ester interchange-reacted with an aryl ester of a lower fatty acid, as disclosed in Japanese Examined Patent Publication No. 56-2,541 and No. 57-47,658 are known.

However, the method (1) in which oxalic acid and the phenol compound are directly esterified to produce a diaryl oxalate is disadvantageous that the reaction rate is extremely low and thus a long reaction time is necessary. Therefore the method (1) is not satisfactory from the viewpoint of industry. Also, the methods (2) and (3) in which a dialkyl oxalate is reacted with a diaryl carbonate or with an aryl ester of a lower fatty acid to produce an aryl oxalate, are not industrially satisfactory, because method (2) or (3) is disadvantageous in that the production of a starting compound consisting of the diaryl carbonate or aryl ester of lower fatty alcohol is difficult, and therefore the starting compound is expensive and difficult to obtain; and various by-products other than the target compound are produced in a large amount, and thus very complicated and troublesome refining process is necessary to isolate the diaryl oxalate.

DISCLOSURE OF THE INVENTION

An object of the present invention is to provide a process for producing a diaryl oxalate by using an alkylaryl oxalate as a starting material, with a high productivity and a high industrial applicability.

The above-mentioned object can be attained by the process of the present invention. The process for producing a diaryl oxalate in accordance with the present invention is characterized in that an alkylaryl oxalate is subjected to a disproportionation reaction in the presence of a disproportionation catalyst, thereby to produce a diaryl oxalate, while removing a by-product comprising a dialkyl oxalate.

Also, in the process for producing a diaryl oxalate of the present invention, a dialkyl oxalate and a phenol compound are subjected to an ester interchange reaction in the presence of an ester interchange catalyst, thereby to produce an alkylaryl oxalate, while removing a by-product comprising an aliphatic alcohol; and the resultant reaction mixture containing the alkylaryl oxalate is subjected to disproportionation using the above-mentioned ester interchange catalyst contained in the reaction mixture, as a disproportionation catalyst, thereby to produce a diaryl oxalate, while removing a by-product comprising a dialkyl oxalate.

BEST MODE OF CARRYING OUT THE INVENTION

Figure 1:
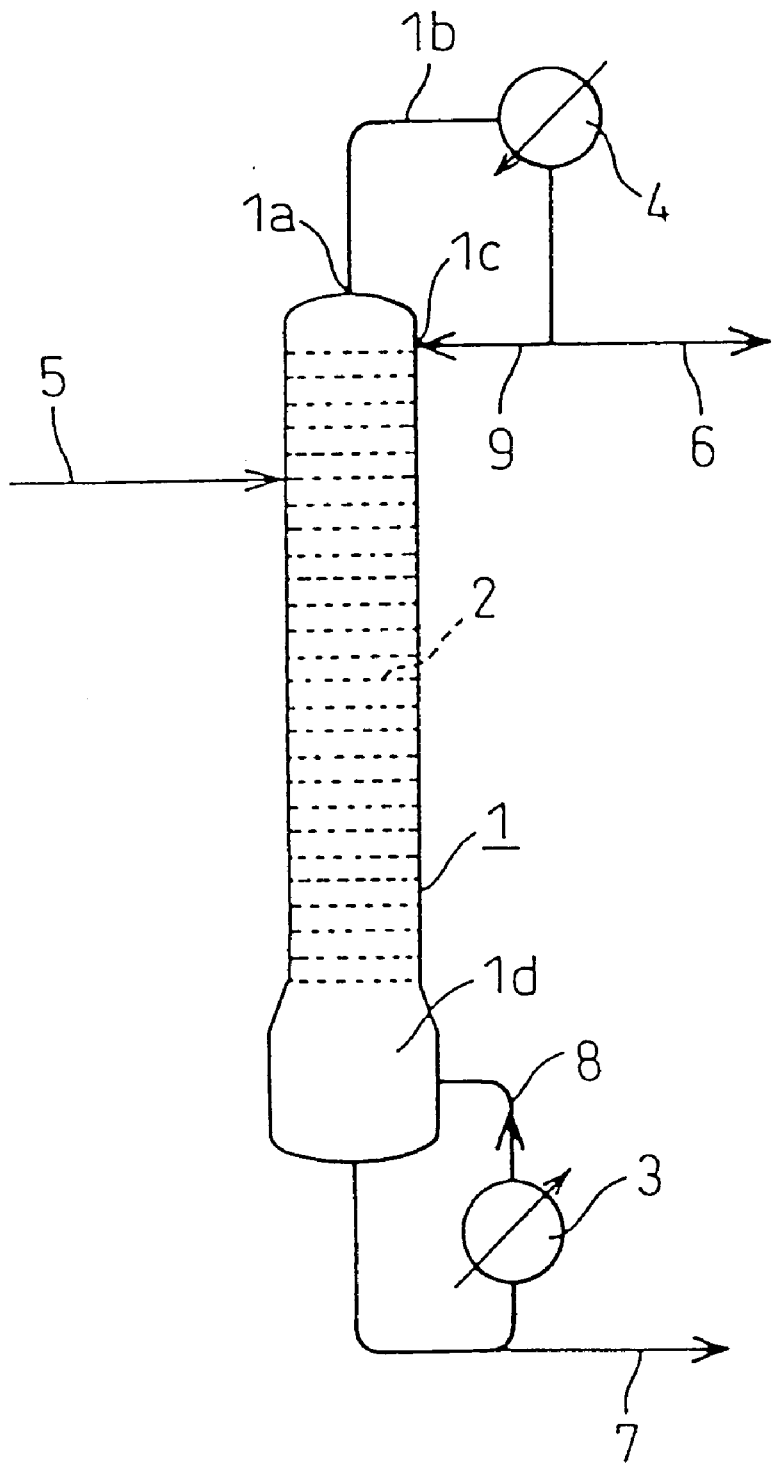
FIG. 1 is an explanatory diagram of procedures for operating an embodiment of the production process of the present invention.

In the process of the present invention, the disproportionation reaction of a starting compound consisting of an alkylaryl oxalate (a) causes a diaryl oxalate (b) and a dialkyl oxalate (c) to be produced as shown in the following reaction formula (1).

Reaction formula (1):

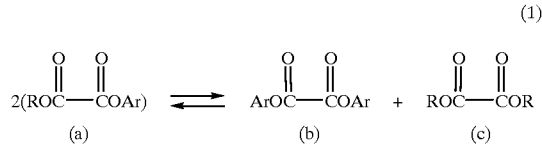

In the formula (1), R represents an alkyl group, preferably a $C_1$ to $C_{10}$ alkyl group, Ar represents an aryl group, preferably a phenyl group or a substituted phenyl group with at least one substituent selected from $C_1$ to $C_6$ alkyl groups, $C_1$ to $C_6$ alkoxyl groups, a nitro group, halogen atoms, and others.

The disproportionation reaction of the alkylaryl oxalate in accordance with the above-mentioned reaction formula (1) is preferably carried out in a liquid state, and as a result, the obtained reaction mixture mainly comprises non-reacted starting material, for example, methylphenyl oxalate (MPO), the disproportionation catalyst, the target compound, for example, diphenyl oxalate (DPO) and a by-product dialkyl oxalate, for example, dimethyl oxalate (DMO). The target compound, for example, diphenyl oxalate can be easily isolated and collected from the above-mentioned reaction mixture, by a conventional method, for example, a distillation method.

The alkylaryl oxalate (a) usable as a starting material for the production process of the present invention, can be produced by subjecting a dialkyl oxalate (c) and a phenol compound (d) to an ester interchange reaction, and removing a by-product aliphatic alcohol (e), in accordance with the following reaction formula (2).

Reaction formula (2):

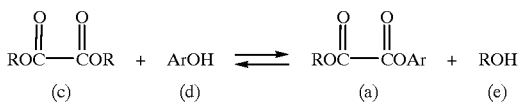

In the formula (2), R and Ar are as defined above.

Additionally, the alkylaryl oxalate (a) can be subjected to an ester interchange reaction of an alkylaryl oxalate with a phenol compound in accordance with the reaction formula (3), to produce a target compound consisting of a diaryl oxalate and a by-product aliphatic alcohol. However, the ester interchange reaction of the reaction formula (3) is disadvantageous in a low reaction rate and thus is not suitable for practical use.

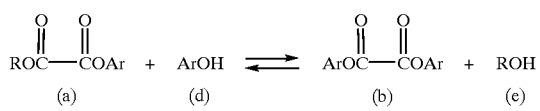

In the formula, R and Ar are as defined above.

In the reaction formulae (1), (2) and (3), $C_1$ to $C_{10}$ alkyl groups represented by R can be selected from methyl, ethyl, n-propyl, iso-propyl, n-butyl, iso-butyl, n-pentyl, iso-pentyl, n-hexyl, iso-hexyl, n-octyl, iso-octyl groups, etc.

Also, in the reaction formulae (1) to (3), when the substituted phenyl groups represented by Ar have a $C_1$ to $C_6$ alkyl group as a substituent, the $C_1$ to $C_6$ alkyl group can be selected from methyl, ethyl, n- and iso-propyl, n-and iso-butyl, n- and iso-pentyl, and n- and iso-hexyl groups. Also when the substituent is a $C_1$ to $C_6$ alkoxyl group, the alkoxyl group can be selected from methoxy, ethoxy, propoxy and butoxy groups.

Also, the aliphatic alcohol (e) produced by the above-mentioned ester interchange reactions corresponds to the R group and includes methanol, ethanol, propanol, butanol, hexanol, etc.

In the disproportionation reaction of the production process of the present invention, the amount of the disproportionation catalyst used is variable in response to the type of the catalyst, the type and size of reaction apparatus, for example, multi tray type distillation column, the types and concentrations of the reaction materials and conditions of the disproportionation reaction. Usually, the catalyst is used preferably in an amount of about 0.0001 to 50% by weight, particularly 0.001 to 30% by weight, more preferably 0.005 to 10% by weight, based on the weight of the alkylaryl oxalate used for the reaction.

In the disproportionation reaction of the process of the present invention, the concentration (C) of the disproportionation catalyst in the starting material mixture or the reaction mixture is preferably about 0.001 to 45% by weight, especially 0.005 to 25% by weight, more preferably 0.01 to 10% by weight, based on the starting material mixture containing alkylaryl oxalate, etc, or the reaction mixture containing the reaction products.

In the disproportionation reaction of the production process of the present invention, there is no specific limitation to reactive conditions. Usually, the reaction temperature may be about 50 to 350° C., the reaction pressure may be 0.001 mmHg to 10 kg/cm², and the reaction time (in the case where a distillation column type reaction apparatus is used, it refers to the residence time of the reaction liquid in the column) may be about 0.001 to 100 hours.

As mentioned above, the alkylaryl oxalate usable for the disproportionation reaction of the production process of the present invention is represented by the formula (a).

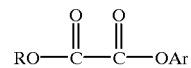

In this formula, R represents an alkyl group, preferably a $C_1$ to $C_{10}$ alkyl group, more preferably a $C_1$ to $C_6$ alkyl group, still more preferably a $C_1$ to $C_4$ alkyl group, and Ar represents an aryl group, preferably a phenyl group, or a phenyl group having one or more substituents. The substituents of the phenyl group are preferably selected from $C_1$ to $C_6$ alkyl groups, $C_1$ to $C_6$ alkoxyl groups, a nitro group and halogen atoms, as mentioned above.

In the process of the present invention, particular examples of the alkylaryl oxalate to be subjected to disproportionation include alkylphenyl oxalates, for example, methylphenyl oxalate, ethylphenyl oxalate, propylphenyl oxalate, butylphenyl oxalate, hexylphenyl oxalate, pentylphenyl oxalate, and octylphenyl oxalate; and alkyl-substituted phenyl oxalates, for example, methyl(p-methylphenyl) oxalate, methyl(p-ethylphenyl) oxalate, ethyl (p-methylphenyl) oxalate, ethyl(p-ethylphenyl) oxalate, methyl(p-methoxyphenyl) oxalate, methyl(p-ethoxypheriyl) oxalate, methyl(p-nitrophenyl) oxalate, and methyl(p-chlorophenyl) oxalate. These alkylaryl oxalates can be synthesized by the ester interchange reaction of the above-mentioned dialkyl oxalate with the phenol compounds.

The alkylaryl oxalates usable for the disproportionation reaction of the process of the present invention are preferably selected from diesters of oxalic acid having an ester structure having an alkyl group with 1 to 4 carbon atoms and an ester structure having a phenyl group (having no substituent), more preferably from lower alkylphenyl esters of oxalic acid, particularly methylphenyl oxalate, ethylphenyl oxalate, propylphenyl oxalate and butylphenyl oxalate.

The diaryl oxalate obtained by the production process of the present invention may be those represented by the compound (b) in the above-mentioned reaction formula (1), preferably, diphenyl oxalate, bis(p-methylphenyl) oxalate, bis(p-methoxyphenyl) oxalate, bis(p-nitrophenyl) oxalate and bis(p-chlorophenyl) oxalate, more preferably diphenyl oxalate.

With respect to the catalysts usable for the disproportionation reaction of the production process of the present invention, there is no specific limitation to type and composition thereof, as long as these catalysts enable the dialkyl oxalate ester and the diaryl oxalate ester to be produced from an alkylaryl oxalate, for example, an alkylphenyl oxalate, by the disproportionation reaction thereof.

In the process of the present invention, the catalyst usable for the disproportionation can be selected from, for example, conventional ester interchange catalysts which are usable for ester interchange reaction of dialkyl esters of dicarboxylic acids with phenol compounds. Also, the disproportionation catalyst usable for the present invention is preferably soluble in a disproportionation system such as a reaction mixture containing the alkylaryl oxalate and/or the target compound.

In the process of the present invention, the particular examples of the ester interchange catalysts usable as a disproportionation catalyst include compounds and complexes of alkali metals, cadmium and zirconium, lead-containing compounds, copper group metal-containing compounds, iron-containing compounds, zinc-containing compounds, organic tin compounds, and Lewis acid compounds of aluminum, titanium and vanadium, and at least one type of soluble catalyst selected from the above-mentioned compounds can be used.

The above-mentioned compounds and complexes of alkali metals, cadmium and zirconium include lithium carbonate, sodium carbonate, potassium carbonate, dibutylaminolithium, lithium diacetylacetonate chelate, cadmium diacetylacetonate chelate, zirconium diacetylacetonate chelate and zirconocene.

The above-mentioned lead-containing compounds include lead sulfides, lead hydroxides, plumbates such as calcium plumbate, lead carbonates and basic salts thereof, organic acid salts of lead and carbonate salts or basic salts thereof, alkyl or aryl lead compounds, for example, tetrabutyl lead, tetraphenyl lead, tributyl lead halogens, triphenyl lead bromine and triphenyl lead, and alkoxy or aryloxy lead compounds, for example, dimethoxylead, methoxyphenoxylead and diphenoxylead.

The above-mentioned copper group metal compounds include copper compounds including copper salts of organic acids, for example, copper acetate, copper diacetylacetonate chelate, and copper oleate, alkylcopper compounds, for example, butyl copper, alkoxycopper compounds, for example, dimethoxycopper, and copper halides, and silver compounds including silver nitrate, silver bromide, and silver picrate. Also, the above-mentioned iron-containing compounds include iron hydroxides, iron carbonates, triacetoxyiron, trimethoxyiron and triphenoxyiron. Further, the zinc-containing compounds include zinc diacetylacetonate chelate, diacetoxyzinc, dimethoxyzinc, diethoxyzinc and diphenoxyzinc.

The above-mentioned organic tin compounds include, for example, $(Ph)_4Sn$, $(OCOCH_3)_4Sn$, $(MeO)_4Sn$, $(EtO)_4Sn$, $(PhO)_4Sn$, $(Me)_3SnOCOCH_3$, $(Et)_3Sn(OCOCH_3)$, $(Bu)_3Sn(OCOSH_3)$, $(Et)_3Sn(OPh)$, $(Me)_3SnOCOPh$, $(Ph)_3Sn(OMe)$, $(Ph)_3SnOCOCH_3$, $(Bu)_2Sn(OCOCH_3)_2$, $(Bu)_2Sn(OMe)_2$, $(Bu)_2Sn(OEt)_2$, $(Bu)_2Sn(OPh)_2$, $(Bu)_2SnCl_2$, $(Ph)_2Sn(OMe)_2$, $(Bu)_2SnO$, $BuSnO(OH)$, $(Et)_3SnOH$ and $(Ph)_3SnOH$.

The above-mentioned Lewis acid compounds of aluminum include, for example, $Al(X)_3$, $Al(OCOCH_3)_3$, $Al(OMe)_3$, $Al(OEt)_3$, $Al(OBu)_3$ and $Al(OPh)_3$. The above-mentioned Lewis acid compounds of titanium include, for example, $Ti(X)_3$, $Ti(OCOCH_3)_3$, $Ti(OMe)_3$, $Ti(OEt)_3$, $Ti(OBu)_3$, $Ti(OPh)_3$, $Ti(X)_4$, $Ti(OCOCH_3)_4$, $Ti(OMe)_4$, $Ti(OEt)_4$, $Ti(OBu)_4$ and $Ti(OPh)_4$. The above-mentioned Lewis acid compounds of vanadium include for example, $VO(X)_3$, $VO(OCOCH_3)_3$, $VO(OMe)_3$, $VO(OEt)_3$, $VO(OPh)_3$ and $V(X)_5$. In the chemical formulae, $COCH_3$ represents a acetyl group, Me represents a methyl group, Et represents an ethyl group, Bu represents a butyl group, Ph represents a phenyl group and X represents a halogen atom.

Among the disproportionation catalysts usable for the production process of the present invention, the use of lithium compounds and complexes thereof, zirconium complexes, organic tin compounds, and titanium Lewis acid compounds is particularly preferred, especially the use of the organic tin compounds and titanium Lewis acid compounds is more preferred.

In the production process of the present invention, the disproportionation reaction of the alkylaryl oxalate can be carried out in the presence of a phenol compound. In this case, the usable weight ratio of the alkylaryl oxalate ester to the phenol compound is established preferably so that the molar ratio of the alkylaryl oxalate to the phenol compound contained in the feed materials is 1:0.01 to 1:1000, more preferably 1:0.1 to 1:100, still more preferably 1:0.5 to 1:20.

The phenol compound which may be present in the disproportionation of the production process of the present invention can be selected from those usable for the ester interchange reaction of the dialkyl oxalate with the phenol compound, which reaction will be explained hereinafter.

The reaction apparatus usable for the production process of the present invention is not limited to a specific apparatus, as long as the disproportionation of the alkylaryl oxalate can be carried out while immediately removing a dialkyl oxalate having a low boiling temperature and produced as a by-product from the reaction mixture. Particularly, the distillation column type reaction apparatus is preferably an apparatus enabling both the disproportionation reaction of the alkylphenyl oxalate in liquid phase and the removal of the by-product dialkyl oxalate by evaporation to be effected. As a distillation column type reaction apparatus as mentioned above, for example, a reaction apparatus (continuous or batch type apparatus) containing a multi-step distillation column are preferably employed.

The above-mentioned reaction apparatus containing the multi-step distillation column is preferably a reaction apparatus containing a 5 to 100 step, more preferably a 7 to 50 step distillation column, which apparatus is also referred to as reactive distillation column.

In the production process of the present invention, the above-mentioned multi-step distillation column-type reaction apparatus may be selected from those having a tray type distillation column in which foam bell trays, perforated plate trays or bubbling trays are arranged, or a packing type distillation column in which various packings, for example, Raschig rings, leschig rings or pall rings, are packed. Also, a reaction apparatus containing both the tray type and packing type distillation columns can be used for the disproportionation reaction of the process of the present invention.

The production process of the present invention will be further explained with reference to the attached drawings. In the inside of the reaction apparatus comprising a multi-step distillation column 1 having a plurality of trays 2 as shown, for example, in FIG. 1 (especially in the portion in which the trays 2 are arranged in the multi-tray distillation column 1), an alkylaryl oxalate fed through a material-feeding line 5 is heated to a desired temperature and subjected to an disproportionation reaction as represented by the reaction formula (1) in the presence of a disproportionation catalyst, a by-product having a low boiling temperature, for example, a dialkyl oxalate is withdrawn by distillation through a withdrawing line 1b connected to a top portion 1a of the distillation column, and optionally the withdrawn vapor is condensed by a cooler 4. In this case, the condensed liquid may be returned into a top portion 1c of the multi-step distillation column through a recycling line 9.

In this case, the reflux ratio is preferably 20 or less, more preferably 10 or less. Also, in this case, a portion or all of the condensed liquid condensed in the cooler 4, which liquid comprises mainly dialkyl oxalate, is preferably discharged to the outside of the system through a withdrawing line 6.

The materials and the catalyst to be fed to the disproportionation reaction of the production process of the present invention are fed in liquid phase through a material feed line 5. The material feed line 5 is preferably connected to the multi-step distillation column 1 at a location in the tray-arranged portion and between a tray located in a position of about ¼ of the total number of the trays above the lowest tray and a tray located in a position of about 1/20 of the total number of the trays below the highest tray, more preferably at a location between a central tray and a tray located in a position of about 1/10 of the total number of the trays below the highest tray.

The liquid material mixture (or a liquid reaction mixture) flows downward through the trays 2 in the distillation portion of the first reactive distillation column 1 and subjected to disproportionation in each tray portion (distillation portion) and in the bottom portion of the column, whereby a reaction liquid containing a diaryl oxalate in a high concentration is accumulated in the bottom id of the second reactive distillation column 1. During this step, a low boiling temperature fraction containing a by-product dialkyl oxalate ester evaporates on each tray 2, and the resultant vapor is introduced into upper trays. The concentration of the dialkyl oxalate in the vapor phase increases with rise of the vapor toward the upper trays, and the resultant refined vapor is separated and removed from the reaction system.

In the multi-step distillation column 1 shown in FIG. 1, the heating of the reaction liquid is carried out by heating the reaction liquid accumulated in the bottom portion of the multi-step distillation column 1 by a heater 3 arranged in a circulating line 8, and circulating the heated liquid along the circulating line 8. Also, a liquid reaction mixture containing a target diaryl oxalate is withdrawn to the outside of the reaction system through a withdrawing line 7, and introduced into a refining step (not shown) wherein the diaryl oxalate is isolated and recovered.

When the disproportionation of the production process of the present invention is carried out while the reaction mixture in liquid state flows downward through the multi-step distillation column, it is preferable that the reaction temperature is equal to or higher than a temperature at which the reaction mixture consisting of a mixture comprising the starting materials and the reaction products, and that the target diaryl oxalate does not thermally decompose at the reaction temperature. The reaction temperature of the disproportionation reaction of the process of the present invention is preferably about 50 to 350° C., more preferably 80 to 300° C., still more preferably 100 to 280° C.

In the process of the present invention, the reaction pressure of the disproportionation may be a reduced pressure, ambient atmospheric pressure or increased pressure. Preferably, the disproportionation reaction is carried out at a temperature and under a pressure which enable the by-product dialkyl oxalate to be removed by evaporation. For example, when the reaction temperature is about 50 to 350° C., the reaction pressure is preferably 0.01 mmHg to 2 kg/cm$^2$, more preferably 0.1 mmHg to 1 kg/cm$^2$, still more preferably 50 to 500 mmHg.

The reaction time of the disproportionation (where the multi-step distillation column is used, the reaction time is equal to a residence time in the distillation column) is variable depending on the reaction conditions and the type and operation conditions of the reaction apparatus. Usually, when the reaction temperature is about 50 to 350° C., the reaction time is preferably about 0.01 to 50 hours, more preferably 0.02 to 10 hours, still more preferably 0.05 to 5 hours.

In an embodiment of the production process of the present invention, it is preferable that the reaction conditions (reaction temperature (T), the residence time (H) of the reaction liquid, and the concentration (C) of the disproportion catalyst in the reaction liquid) are appropriately adjusted so as to satisfy the two requirements that the diaryl oxalate must be produced in a sufficient amount (a high yield) by the above-mentioned disproportionation, and that the produced diaryl oxalate must not be consumed by a decomposition or polymerization thereof due to a thermal history of a high temperature for a long time, at a high proportion (decomposition percentage) of, for example, 1 to 5% by weight. Particularly, the above-mentioned requirements are important for industrial practice of the process of the present invention.

In the process of the present invention, where the disproportionation of the alkylaryl oxalate is carried out by controlling the disproportionation reaction temperature (T) of the alkylaryl oxalate in a range of from 100° C. to 280° C., and adjusting the concentration of the disproportionation catalyst (C: catalyst concentration in the reaction liquid) to 0.001 to 45% by weight, (a) when the disproportionation reaction temperature (T) is 100° C. or more but less than 220° C., the residence time (H) of the reaction liquid at this temperature is controlled to 0.01 to 10 hours, preferably 0.05 to 5 hours, (b) when the disproportionation reaction temperature (T) is 220° C. or more but less than 250° C., the residence time (H) of the reaction liquid at this temperature is controlled to 0.01 to 2 hours, preferably 0.05 to 1 hours, and (c) when the disproportionation reaction temperature (T) is 250° C. or more but not exceeding 280° C., the residence time (H) of the reaction liquid at this temperature is controlled to 0.01 to 0.5 hours, preferably 0.05 to 0.2 hours, thereby to cause the yield of the product by the disproportionation reaction of the alkylaryl oxalate to be maintained at a satisfactory level and the loss (consumption) of the diaryl oxalate ester by the above-mentioned thermal history to be prevented.

Also, in the present invention, it is industrially preferred that the disproportionation reaction temperature (T) is 120° C. or more but less than 220° C., particularly 125° C. to 215° C., the disproportionation catalyst concentration (C: catalyst concentration in the reaction liquid) is 0.005 to 25% by weight, particularly, 0.01 to 10% by weight, more particularly 0.05 to 5% by weight, and the residence time (H) of the reaction liquid at the temperature is 0.05 to 10 hours, particularly 0.05 to 5 hours, more particularly 0.1 to 5 hours.

In the production process of the present invention, if the reaction conditions fall outside of the upper limits of the above-mentioned conditions, a decomposition and/or polymerization of the target diaryl oxalate ester in the reaction liquid may occur to a large extent and result in loss of the target product, and thus such reaction conditions are not industrially preferred. Also, if the reaction conditions fall outside of the lower limits of the above-mentioned conditions, the rate of the disproportionation reaction may decrease and thus the reaction may not be completed within a practical process time, and thus such reaction conditions are not preferable.

In the production process of the present invention, in the case where the alkylaryl oxalate is produced by an ester interchange-reaction of the dialkyl oxalate with the phenol compound, and then the resultant reaction liquid is subjected to the disproportionation reaction to disproportionate the alkylaryl oxalate in the reaction liquid, the diaryl oxalate can be produced by firstly carrying out the ester interchange reaction of the dialkyl oxalate with the phenol compound in the presence of an ester interchange catalyst, while removing the by-product aliphatic alcohol, thereby to produce the alkylaryl oxalate such as an alkylphenyl oxalate; and then carrying out the disproportionation reaction of the alkylaryl oxalate in the above-mentioned manner.

In the above-mentioned ester interchange reaction, for example, when a dialkyl oxalate (c) and a phenol compound (d) are reacted with each other by the ester interchange reaction in accordance with the above-mentioned reaction formula (2), an alkylaryl oxalate (a) and an aliphatic alcohol (e) are produced. Also, during this ester interchange reaction, another reaction in which the produced alkylaryl oxalate (a) is further disproportionated in accordance with the above-mentioned reaction formula (1), occurs to produce the diaryl oxalate. Further, during the ester interchange reaction, still another reaction in which the produced alkylaryl oxalate (a) and the phenol compound (d) are further reacted with each other in accordance with the above-mentioned reaction formula (3) occurs to produce the diaryl oxalate (b). These reactions are preferably carried out in a liquid phase. Also, each of the reactions is an equilibrium reaction, and the equilibrium point between the original system and the reaction product system is close to the original system.

The above-mentioned dialkyl oxalate is preferably selected from diesters of oxatic acid provided with two ester structures each having an alkyl group with 1 to 10 carbon atoms, preferably 1 to 6 carbon atoms, more preferably 1 to 4 carbon atoms, for example, dimethyl oxalate, diethyl oxalate, dipropyl oxalate, dibutyl oxalate, dihexyl oxalate, dioctyl oxalate, and methylethyl oxalate. Particularly when a dialkyl oxalate of which each alkyl group has 1 to 4 carbon atoms is used in the production process of the present invention, the aliphatic alcohol produced as a by-product of the ester interchange reaction can be easily removed. Especially, dimethyl oxalate, diethyl oxalate, dipropyl oxalate and dibutyl oxalate are preferably employed.

The phenol compounds usable for the above-mentioned ester interchange reaction include phenol and substituted phenol compounds which may have at least one substituent selected from alkyl groups with 1 to 6 carbon atoms, alkoxyl groups with 1 to 6 carbon atoms, a nitro group and halogen atoms. The most preferable one is phenol. In the process of the present invention, the phenol compounds different from phenol include alkylphenols, for example, o-, m- or p-cresol, xylenols(dimethylphenol), dipropylphenols, methylethyl phenols, trimethylphenols, tetramethylphenols, ethyl phenols, propyl phenols, butyl phenols and hexyl phenols; alkoxyl phenols, for example, o-, m- or p-hydroxyanisol and ethoxyphenols; halophenols, for example, p-chlorophenol and 3,5-dibromophenol; and nitrophenols, for example, o-, m- or p-nitrophenol.

The ester interchange catalysts usable for the above-mentioned ester interchange reaction are not limited to specific type of ester interchange catalysts, as long as they can produce the alkylaryl oxalates by the ester interchange reaction of the dialkyl oxalates with the phenol compounds. The ester interchange catalysts include those specifically exemplified as ester interchange catalysts usable for the disproportionation reaction of the alkylphenyl oxalates.

Also, it is preferable that the catalyst used for the ester interchange reaction of the dialkyl oxalate with the phenol compound and the catalyst used for the disproportionation reaction of the alkylphenyl oxalate are preferably of the same group as each other, more preferably the same as each other.

In the above-mentioned ester interchange reaction, for example, when dimethyl oxalate and phenol are used as starting materials, methylphenyl oxalate (MPO) and methyl alcohol are mainly produced in accordance with the reaction formula (2), and small amounts of diphenyl oxalate and dimethyl oxalate are produced in accordance with the reaction formula (1). Further, in accordance with the reaction formula (3), small amounts of diphenyl oxalate (DPO) and methyl alcohol are produced.

In this case, the resultant reaction liquid to be supplied to the next disproportionation reaction step mainly comprises the reaction materials and catalyst used in the ester interchange reaction, the target alkylaryl oxalate ester (for example, MPO) and diaryl oxalate (for example, DPO) and a by-product consisting of methyl alcohol.

In the above-mentioned ester interchange reaction, the weight ratio of the dialkyl oxalate to the phenol compound to be used is variable in response to the type and amount of the catalyst and the reaction conditions. Usually, the molar ratio of the dialkyl oxalate to the phenol compound contained in the feed material is preferably 0.01:1 to 1000:1, particularly and more preferably 0.1:1 to 100:1, more preferably 0.5:1 to 2:1.

The amount of the catalyst to be used for the ester interchange reaction is variable depending on the type of the catalyst, the type and size of the reaction apparatus (for example, multi-tray distillation column), type of each material, composition of the feed material, and reaction conditions of the ester interchange reaction. Usually, the ester interchange reaction catalyst is used preferably in an amount of about 0.0001 to 50% by weight, more preferably 0.001 to 30% by weight, still more preferably 0.005 to 10% by weight, based on the total weight of the dialkyl oxalate and the phenol compound.

There is no limitation to the reaction conditions of the ester interchange reaction. Generally, it is preferable that the reaction temperature is about 50 to 350° C., the reaction pressure is 0.001 mmHg to 200 kg/cm$^2$ and the reaction time is 0.001 to 100 hours.

In the process of the present invention, when the ester interchange reaction and the disproportionation reaction are successively carried out, it is preferred that the reaction conditions (catalyst concentration, reaction temperature, etc.) of the ester interchange reaction are considerably close to the reaction conditions of the successive disproportionation reaction so that the ester interchange reaction conditions do not import any disadvantageous influence on the successive disproportionation reaction.

The reaction apparatus for the ester interchange reaction is not limited to a specific one and may be any type of reaction apparatus, as long as the ester interchange reaction of the dialkyl oxalate with the phenol compound can be carried out while immediately removing the aliphatic alcohol produced as a by-product of the reaction and having a low boiling temperature, from the reaction liquid. Preferably, the distillation column type reaction apparatus enables the ester interchange reaction to be carried out in the reaction liquid in liquid phase while allowing the by-product aliphatic alcohol to be removed. As a distillation column type reaction apparatus as mentioned above, for example, a reaction apparatus comprising a continuous multi-step distillation column similar to that for the above-mentioned disproportionation reaction can be advantageously used. The reaction apparatus comprising the multi-step distillation column preferably has a theoretical number of steps of 2 or more, more preferably 5 to 100, still more preferably 7 to 50.

As a multi-step distillation column type reaction apparatus for the ester interchange reaction, for example, multi-step type distillation columns provided with bubble cap trays, sieve trays or valve trays, or packing type distillation columns in which various packings, for example, Raschig rings, leschig rings or pall rings, are packed, which are similar to those for the disproportionation reaction, can be employed.

Other distillation columns provided with both the trays and the packings can be used.

Figure 2:
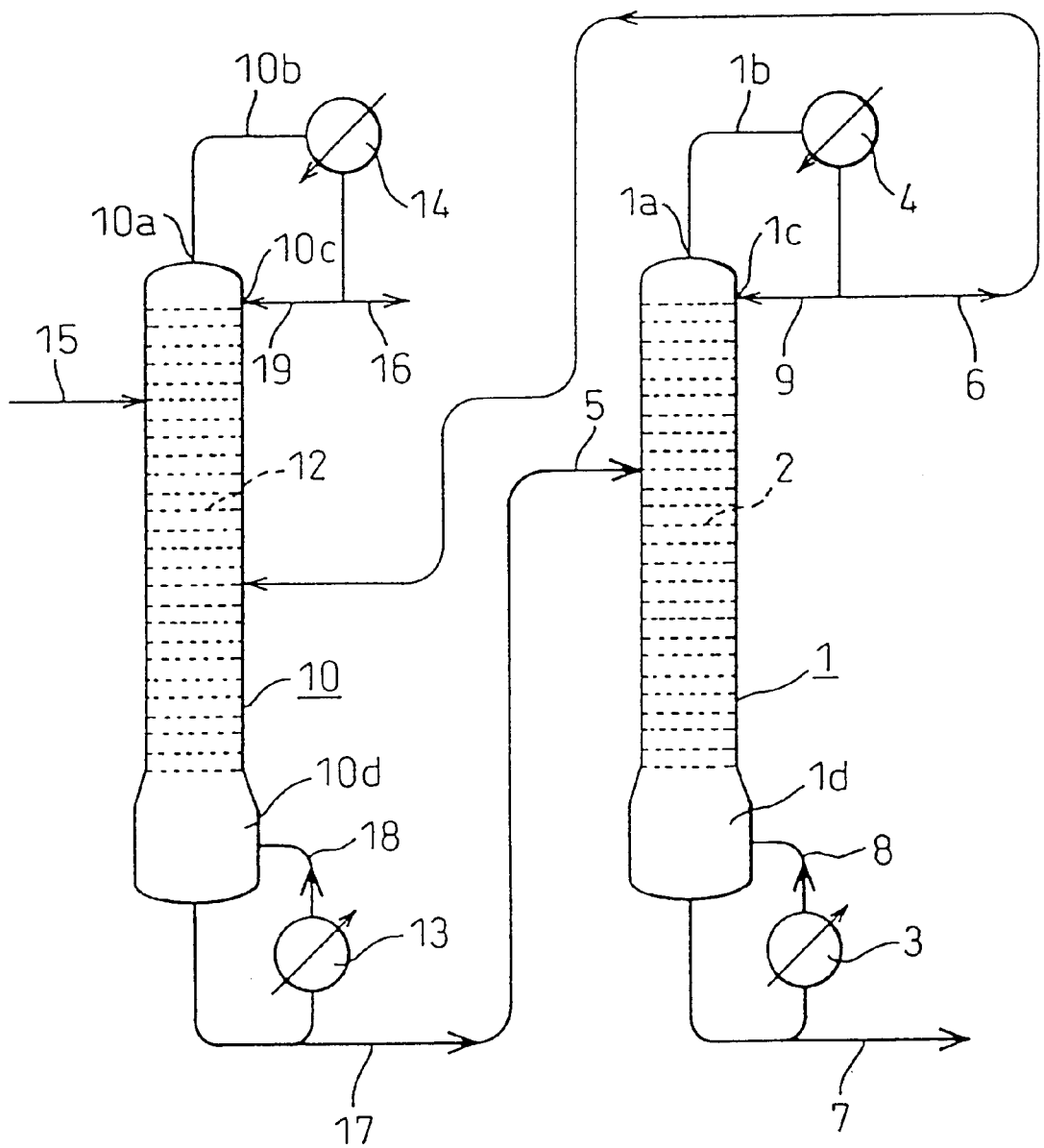
FIG. 2 is an explanatory diagram of procedures for operating another embodiment of the production process of the present invention.

In the process of the present invention a diaryl oxalate can be continuously produced from a dialkyl oxalate and a phenol compound, by using a reaction apparatus as shown in FIG. 2, wherein, in a first reactive distillation column (multi-step distillation column) 10, a dialkyl oxalate and a phenol compound are subjected to an ester interchange reaction in the presence of an ester interchange catalyst, while removing a by-product comprising an aliphatic alcohol by evaporation, and then, in a second reactive distillation column (multi-step distillation column) 1, the above-mentioned ester interchange catalyst is employed again as a disproportionation catalyst, and the resultant alkylaryl oxalate is subjected to a disproportionation reaction, while removing the dialkyl oxalate (mainly a by-product) and the phenol compound by evaporation. This process is industrially preferred.

In the reaction apparatus shown in FIG. 2, the first reactive distillation column (multi-step distillation column) 10 and the second reactive distillation column (multi-step distillation column) 1 are connected to each other through a withdrawing line (conduit) 17 for a liquid fraction in the bottom portion of the first reactive distillation column 10 and through a feed line 5 for the second reactive distillation column 1.

Namely, as shown in FIG. 2, by using the first reactive distillation column 10 and the second reactive distillation column 1, the production of the alkylaryl oxalate by the ester interchange reaction and the production of the diaryl oxalate by the disproportionation reaction can be successively carried out.

In this case, a condensed liquid or vapor of the dialkyl oxalate withdrawn through the withdrawing line 6 of the multi-step distillation column (the second reactive distillation column) 1 for the above-mentioned disproportionation reaction is fed into the multi-step distillation column (the first reactive distillation column) 10 and recycled and re-used.

In the first reactive distillation column 10 shown in FIG. 2, a plurality of distilling trays 12 are arranged, a feed material comprising the dialkyl oxalate, the phenol compound and the ester interchange catalyst is fed into the column 10 through a feed line 15, the ester interchange reaction of the feed material is carried out in the first reactive distillation column 10 and the resultant by-product comprising the aliphatic alcohol is distilled and withdrawn from the column top 10a through a line 10b and condensed by a cooler 14. The resultant condensed liquid is withdrawn to the outside of the system through a line 16. If necessary, a portion of the condensed liquid may be returned to the column top 10c through a line 19. In this case, the reflux ratio is preferably 20 or less, more preferably 10 or less.

The feed line 15 for the starting materials (dialkyl oxalate and phenol compound) and the ester interchange catalyst to be fed to the above-mentioned ester interchange reaction is preferably connected to the multi-step distillation column 10, in the range between a tray located about ¼ of the total number of trays above the lowest tray and a tray located about 1/20 of the total number of trays below the highest tray, more preferably between a central tray and a tray located about 1/10 of the total number of the trays below the highest tray.

When the liquid material mixture (or reaction liquid) flows downward through the trays 12 in the distillation portion of the column 10 and is subjected to the ester interchange reaction on each tray portion (in the distillation portion) and in the bottom portion of the column, a resultant reaction liquid containing the alkylaryl oxalate in a high concentration is accumulated in the bottom portion of the first reactive distillation column 10. Also, a low boiling temperature substance produced as a by-product and containing the aliphatic alcohol is evaporated on each tray and the resultant vapor phase flows upward through the trays.

The concentration of the aliphatic alcohol increases as it rises through the tray portion, and then the refined vapor is separated and removed from the reaction liquid.

In the first reactive distillation column 10 of FIG. 2, the heating of the reaction liquid can be effected by heating the reaction liquid accumulated in the bottom portion of the multi-step distillation column 10 by a heater 13 arranged in a circulating line 18, while circulating the reaction liquid through the circulating line 18. Also, a reaction liquid containing the alkylaryl oxalate produced as an intermediate product is withdrawn to the outside of the system through a withdrawing line 17, and fed into the second reactive distillation column for the disproportionation reaction in the next step through a material feed line 5. In this column, the reaction liquid is subjected to the disproportionation reaction (step) as explained in detail above, to disproportionate the alkylaryl oxalate and thereby to produce the target diaryl oxalate.

When the ester interchange reaction of the reaction liquid in liquid state is carried out while the reaction liquid flows downward through the multi-step distillation column, it is preferable that the reaction temperature is equal to or higher than the melting temperature of the reaction mixture containing the starting materials and the reaction products and is within the temperature range in which the reaction product comprising the alkylaryl oxalate does not thermally decompose. Especially, the reaction temperature of the ester interchange reaction is preferably in the range of from about 50 to 350° C., more preferably 100 to 280° C., still more preferably 125 to 215° C.

EXAMPLES

A referential examples and examples of the present invention will be disclosed below

Referential Example 1 (Preparation of an Alkylaryl Oxalate)

A liquid mixture of phenol, dimethyl oxalate and tetraphenoxytitanium (TPT) in a molar ratio of 1.5:1:0.002 was charged in an amount of 500 ml in a bottom portion (1 liter capacity) of an Oldershaw column (multi-step reactive distillation column). The bottom portion was heated to a temperature of 190° C. under ambient atmospheric pressure by a mantle heater, to create a reflux circulation of the liquid mixture.

Then, a liquid having the same composition as mentioned above was fed in a flow rate of 300 ml/hour into a twelfth tray from the highest tray of the Oldershaw column, the reaction liquid was subjected to a continuous ester interchange reaction for 10 hours, while a generated methyl alcohol vapor was continuously withdrawn from the top of the column and the reaction liquid was continuously withdrawn so as to maintain the amount of the reaction liquid in the bottom of the Oldershaw column at a level of 500 ml, and to adjust the reflux ratio to a level of about 5.

In the ester interchange reaction in the Oldershaw column, the residence time of the reaction liquid was about 2 hours.

While the above-mentioned conditions were maintained, the compositions of the distilled liquid from the top of the Oldershaw column and the withdrawn liquid from the bottom thereof were continuously recorded by gas-chrontatography analysis.

In the ester interchange reaction in the Oldershaw column as mentioned above, the flow rate and the composition (average value) of the reaction liquid between a stage at which the compositions of the distilled liquid and the withdrawn liquid became stable (about 5 hours after from the start of the reaction) and a stage of 10 hours after from the stabilized stage were as follows.

Methyl alcohol with a degree of purity of approximately 100% was distilled at a flow rate of 22.5 g/hour from the top of the Oldershaw column, and a reaction liquid comprising 36.61% by weight of phenol, 24.25% by weight of dimethyl oxalate, 28.97% by weight of methylphenyl oxalate, and 9.83% by weight of diphenyl oxalate was withdrawn at a flow rate of 294 g/hour from the bottom of the Oldershaw column.

Example 1

The ester interchange catalyst and methylphenyl oxalate ester, etc, -containing reaction liquid obtained in Referential Example 1 and containing 36.61% by weight of phenol, 24.25% by weight of dimethyl oxalate, 28.97% by weight of methylphenyl oxalate and 9.83% by weight of diphenyl oxalate was charged in an amount of 800 ml in a bottom portion (one liter capacity) of an Oldershaw column (multi-step reactive distillation column) having a column diameter of 32 mm and 50 plates, the top of the column was connected to a vacuum line, the pressure in the column was reduced to 300 mmHg, and then the bottom of the column was heated to a temperature of about 190° C. by a mantle heater, and a withdrawing operation for the reaction liquid was started without reflux. After the start of the withdrawal, the temperature of the bottom of the Oldershaw column gradually rose.

After the stage at which the amount of the liquid in the bottom of the Oldershaw column reached 500 ml, the reaction liquid of Referential Example 1 was fed at a flow rate of 300 ml/hour to the twelfth step of the Oldershaw column from the highest tray and subjected to a continuous disproportionation reaction for 10 hours, while continuously withdrawing dimethyl oxalate, phenol and a small amount of methyl alcohol evaporated and delivered from the top of the Oldershaw column, and continuously withdrawing the reaction liquid from the bottom so as to maintain the amount of the liquid in the bottom of the Oldershaw column at a level of 500 ml, without returning.

In the disproportionation reaction in the Oldershaw column, the residence time of the reaction liquid was about 4 hours.

While maintaining the above-mentioned conditions, the compositions of the distilled liquid from the top of the Oldershaw column and the withdrawn liquid from the bottom of the Oldershaw column were recorded by gas chromatographic analysis.

In the disproportionation reaction in the Oldershaw column as mentioned above, the flow rate and the composition (average value) of the reaction liquid between a stage at which the compositions of the above-mentioned distilled liquid and withdrawn liquid became stable (about 5 hours after the start of the reaction) and a stage of 10 hours after the stabilizing stage were as follows.

From the top of the Oldershaw column, a low boiling temperature liquid mixture comprising 49.21% by weight of dimethyl oxalate, 50.12% by weight of phenol, 0.53% by weight of methyl alcohol, and 0.25% by weight of methylphenyl oxalate was distilled at a flow rate of 190 g/hr. Also, from the bottom of the Oldershaw column a reaction liquid comprising 13.54% by weight of phenol, 2.55% by weight of dimethyl oxalate, 18.70% by weight of methylphenyl oxalate, and 64.30% by weight of diphenyl oxalate and having a catalyst concentration, in terms of TPT, of about 0.9% by weight was withdrawn at a flow rate of 125 g/hr.

Example 2

A disproportionation reaction was carried out by the same procedures as in Example 1, except that the feed point of the feed material (a mixture of phenol with methylphenyl oxalate and TPT) was changed from the twelfth tray of the Oldershaw column to the bottom thereof.

In the conditions that the compositions of the distilled liquid and the withdrawn liquid were stabilized, the flow rates and compositions of the liquids were as follows.

From the top of the Oldershaw column, a low boiling temperature liquid mixture comprising 53.72% by weight of dimethyl oxalate, 45.62% by weight of phenol, and 0.45% by weight of methyl alcohol was distilled at a flow rate of 117 g/hr. Also, from the bottom of the Oldershaw column a reaction liquid comprising 31.63% by weight of phenol, 10.31% by weight of dimethyl oxalate, 32.90% by weight of methylphenyl oxalate, and 25.41% by weight of diphenyl oxalate and having a catalyst concentration, in terms of TPT, of about 0.55% by weight was withdrawn at a flow rate of 198 g/hr.

Example 3

The reaction liquid obtained in Example 1 was distilled under a reduced pressure of 20 mmHg to remove phenol and dimethyl oxalate, and then further distilled to separate methylphenyl oxalate. Methylphenyl oxalate having a degree of purity of approximately 100% and containing no catalyst was obtained.

A 500 ml three-necked flask equipped with a stirrer, a thermometer and a Wigrue distillation tube having a length of 30 cm was charged with 300 g of the above-mentioned methylphenyl oxalate and 10 g of TPT, and placed in an oil bath. The methylphenyl oxalate was subjected to a disproportionation reaction at a temperature of 180° C. under ambient atmospheric pressure, while withdrawing dimethyl oxalate.

During the time from the start of the withdrawal until about 4 hours after the start of the withdrawal, dimethyl oxalate was withdrawn in an amount of 96 g. The resultant reaction liquid had a catalyst concentration, in terms of TPT, of 0.49% by weight and comprised 0.12% by weight of dimethyl oxalate, 7.73% by weight of methylphenyl oxalate, and 93.07% of diphenyl oxalate.

Example 4

A disproportionation reaction was carried out by the same procedures as in Example 3, except that 1.1 g of zirconium acetylacetonate were used in place of 1.0 g of TPT.

During the time from the start of the withdrawal until about 4 hours after the start of the withdrawal, dimethyl oxalate was withdrawn in an amount of 95 g. The resultant reaction liquid had a catalyst concentration, in terms of zirconium acetylacetonate, of 0.54% by weight and comprised 0.18% by weight of dimethyl oxalate, 9.61% by weight of methylphenyl oxalate, and 91.55% of diphenyl oxalate.

Example 5

A disproportionation reaction was carried out by the same procedures as in Example 3, except that 0.8 g of tetraphenyltin was used in place of 1.0 g of TPT.

During the time from the start of the withdrawal until about 4 hours after the start of the withdrawal, dimethyl oxalate was withdrawn in an amount of 97 g. The resultant reaction liquid had a catalyst concentration, in terms of tetraphenyltin, of 0.39% by weight and comprised 0.09% by weight of dimethyl oxalate, 5.79% by weight of methylphenyl oxalate, and 94.59% of diphenyl oxalate.

Example 6

A disproportionation reaction was carried out by the same procedures as in Example 1, except that the reaction temperature was changed to 200° C., and the residence time of the reaction liquid was changed to about 4.5 hours.

During the time from the start of the withdrawal until about 5 hours after the start of the withdrawal, the reaction liquid having a catalyst concentration of 0.92% by weight in terms of TPT, was withdrawn in an amount of 118 g. The resultant reaction liquid comprised 1.32% by weight of dimethyl oxalate, 20.05% by weight of methylphenyl oxalate, 73.94% of diphenyl oxalate, and 2.2% by weight of phenol.

Example 7

Two Oldershaw columns (multi-step reactive distillation columns) having a column diameter of 32 mm and 50 plates and provided with a bottom with a capacity of one liter were used to assemble a reaction apparatus in which a first reactive distillation column and a second reactive distillation column are connected to each other in the same manner as shown in FIG. 2, except that the withdrawing line 6 for the condensed liquid was not connected to the first reactive distillation column. An ester interchange reaction and a disproportionation reaction were successively carried out by using the above-mentioned reaction apparatus.

First, a bottom portion of an Oldershaw column (multi-step reactive distillation column: first reactive distillation column) was charged with 500 ml of a liquid material mixture in which phenol, dimethyl oxalate and tetraphenoxytitanium (TPT) were mixed in a molar ratio of 1.5:1:0.002, and the bottom portion was heated to a temperature of about 190° C. by a mantle heater so as to create a reflux circulating condition under ambient atmospheric pressure.

Then, a liquid material mixture having the same composition as that mentioned above was fed at a flow rate of 300 ml per hour to a twelfth tray from the highest tray of an Oldershaw column, to carry out an ester interchange reaction, the reflux ratio was established to about 5, methyl alcohol produced and delivered from the top of the column was continuously withdrawn, and the reaction liquid was continuously withdrawn from the bottom of the column so as to maintain the amount of the reaction liquid in the bottom portion at 500 ml. When the compositions of the distilled liquid and the withdrawn liquid was stabilized about 5 hours after the start of the reaction, methyl alcohol with a degree of purity of about 100% was distilled in a flow rate of 22.7 g/hr from the top of the Oldershaw column, a reaction liquid (catalyst concentration: 0.34% by weight) comprising 36.61% by weight of phenol, 25.81% by weight of dimethyl oxalate, 30.74% by weight of methylphenyl oxalate and 6.81% by weight of diphenyl oxalate was withdrawn at a flow rate of 296 g/hr from the bottom of the Oldershaw column, and the withdrawn reaction liquid was stored in an intermediate container for feeding the reaction liquid at a flow rate of 316 g/hr to the second reactive distillation column.

In the above-mentioned ester interchange reaction in the Oldershaw column (first reactive distillation column), the residence time of the reaction liquid was about 2 hours.

Separately, a bottom portion of an Oldershaw column (multi-stage reactive distillation column), as a second reactive distillation column, was charged with 800 ml of the reaction liquid obtained in Referential Example 1 and containing the ester interchange catalyst, methylphenyl oxalate, etc., the reaction liquid was heated to a temperature of about 190° C. by a mantle heater, and the withdrawal of the reaction liquid was started without reflux. After the start of the withdrawal, the temperature of the liquid mixture in the bottom portion of the Oldershaw column (the second reactive distillation column) gradually rose.

When the amount of the bottom liquid in the Oldershaw column (the second reactive distillation column) reached 500 ml, the feed of the reaction liquid (ester interchange reaction liquid) withdrawn from the bottom portion of the first reactive distillation column was started at a flow rate of 300 ml per hour to the twelfth tray from the highest tray of the Oldershaw column (the second reactive distillation column), and the fed reaction liquid was subjected to a continuous disproportionation reaction at a temperature of 190° C. for 10 hours, while continuously withdrawing dimethyl oxalate, phenol and a small amount of methyl alcohol delivered from the top of the column, without reflux, and while continuously withdrawing the reaction liquid (disproportionation reaction liquid) from the bottom of the second reactive distillation column so as to maintain the amount of the liquid in the bottom portion of the Oldershaw column (the second reactive distillation column) at a level of 500 ml.

In the disproportionation reaction in the Oldershaw column (the second reactive distillation column), the residence time of the reaction liquid was about 4 hours.

While maintaining the above-mentioned conditions, the compositions of the distilled liquid from the top and the withdrawn liquid from the bottom of the Oldershaw column (the second reactive distillation column) was continuously recorded by gas chromatographic analysis.

In the above-mentioned disproportionation reaction in the Oldershaw column (the second reactive distillation column), during the time between a stage at which the compositions of the distilled liquid and the withdrawn liquid reached a stable condition, and a stage of 10 hours after the stabilized stage, the distilled liquid and the withdrawn liquid had the following flow rates and compositions (average values).

The distilled liquid from the top of the Oldershaw column (the second reactive distillation column) had the following composition.

| Dimethyl oxalate | 49.80% by weight |
|---|---|
| Phenol | 49.52% by weight |
| Methyl alcohol | 0.50% by weight |
| Methylphenyl oxalate | 0.18% by weight |

The distilled liquid was delivered at a flow rate of about 190 g/hr.

Also, the withdrawn reaction liquid from the bottom of the Oldershaw column (the second reactive distillation column) had the following composition.

| Phenol | 12.88% by weight |
|---|---|
| Dimethyl oxalate | 1.49% by weight |
| Methylphenyl oxalate | 19.55% by weight |
| Diphenyl oxalate | 65.21% by weight |

The reaction liquid (catalyst concentration: about 0.90% by weight) was withdrawn at a flow rate of 124 g/hr.

Industrial Applicability

The present invention provides, for the first time, a process for industrially producing a diaryl oxalate (especially diphenyl oxalate) which is important as a material for chemical reactions, from an alkylaryl oxalate (especially methylphenyl oxalate) by a disproportionation reaction.

In the production process of the present invention, the kinds of by-products are fewer than those in conventional processes for producing the diaryl oxalate and the target diaryl oxalate can be easily isolated and refined.

We claim:

1. A process for producing a diaryl oxalate, characterized in that an alkylaryl oxalate is subjected to a disproportionation reaction in the presence of a disproportionation catalyst, thereby to produce a diaryl oxalate, while removing a by-product comprising a dialkyl oxalate.

2. The process for producing a diaryl oxalate as claimed in claim 1, wherein a dialkyl oxalate and a phenol compound are subjected to an ester interchange reaction in the presence of an ester interchange catalyst, thereby to produce an alkylaryl oxalate, while removing a by-product comprising an aliphatic alcohol, and the resultant reaction mixture containing the alkylaryl oxalate is subjected to a disproportionation reaction for which the ester interchange catalyst contained in the reaction mixture is used as a disproportionation catalyst, thereby to produce a diaryl oxalate, while removing a by-product comprising dialkyl oxalate.

3. The process for producing a diaryl oxalate as claimed in claim 1 or 2, wherein the removal of the by-product dialkyl oxalate and the disproportionation reaction of the alkylaryl oxalate are carried out in a reaction apparatus comprising a reactive distillation column.

4. The process for producing a diaryl oxalate as claimed in claim 2, wherein in a first reactive distillation column, the ester interchange reaction of the dialkyl oxalate with the phenol compound is carried out and the by-product aliphatic alcohol is removed by evaporation, and then in a second reactive distillation column, the alkylaryl oxalate is subjected to the disproportionation reaction and the dialkyl oxalate and the phenol compound contained in the reaction mixture are removed by evaporation.

5. The process for producing a diaryl oxalate as claimed in claim 4, wherein a vapor containing the dialkyl oxalate and the phenol compound removed by evaporation from the second reactive distillation column is liquefied by cooling, the resultant liquid mixture is returned to the first reactive distillation column and subjected to the ester interchange reaction.

6. The process for producing a diaryl oxalate as claimed in claim 4, wherein at least one of the first reactive distillation column and the second reactive distillation column has a distillation column provided with a plurality of trays.

7. The process for producing a diaryl oxalate as claimed in claim 1 or 2, wherein the disproportionation catalyst to be used for the disproportionation reaction contains at least one compound selected from compounds and complexes of alkali metals, cadmium and zirconium, lead-containing compounds, iron-containing compounds, copper-group metal-containing compounds, zinc-containing compounds, organic tin compounds, aluminum-containing Lewis acid compounds, titanium-containing Lewis acid compounds, arid vanadium-containing Lewis acid compounds and is soluble in the disproportionation reaction system.

8. The process for producing a diaryl oxalate as claimed in claim 1 or 2, wherein the disproportionation reaction is carried out in the reactive distillation column, the concentration (C) of the disproportion action catalyst contained in the reaction mixture in the reactive distillation column is controlled to a range of from 0.001 to 45% by weight, and the temperature (T) of the disproportionation reaction is controlled to a range of from 100 to 280° C.

9. The process for producing a diaryl oxalate as claimed in claim 8, wherein in the disproportionation reaction of the alkylaryl oxalate in the disproportionation reactive distillation column, (a) when the disproportionation reaction temperature (T) is 100° C. or more but less than 220° C., the residence time (H) of the reaction mixture in the disproportionation reactive distillation column is controlled to 0.01 to 10 hours, (b) when the disproportionation reaction temperature (T) is 220° C. or more but less than 250° C., the residence time (H) of the reaction mixture in the disproportionation reactive distillation column is controlled to 0.01 to 2 hours, and (c) when the disproportionation reaction temperature (T) is 250° C. more but not exceeding 280° C., the residence time (H) of the reaction mixture in the disproportionation reactive distillation column is controlled to 0.01 to 0.5 hours.

10. The process for producing a diaryl oxalate as claimed in claim 8, wherein in the disproportionation reaction of the alkylaryl oxalate in the disproportionation reactive distillation column, the disproportionation reaction temperature (T) is controlled to 125° C. to 215° C., the concentration of the disproportionation catalyst in the reaction mixture is controlled to 0.005 to 25% by weight, and the residence time of the reaction mixture in the disproportionation reactive distillation column is controlled to 0.01 to 10 hours.

* * * * *